(12) United States Patent
Lahti et al.

(10) Patent No.: US 10,011,086 B2
(45) Date of Patent: Jul. 3, 2018

(54) PEEL-OPEN PACKAGE

(71) Applicant: BEMIS COMPANY, INC., Neenah, WI (US)

(72) Inventors: Hanna-Mari Lahti, Lempaala (FI); Merja H. Savola, Parola (FI); Christopher R. Jansen, Kaukauna, WI (US)

(73) Assignee: Bemis Company, Inc., Neenah, WI (US)

( * ) Notice: Subject to any disclaimer, the term of this patent is extended or adjusted under 35 U.S.C. 154(b) by 0 days.

(21) Appl. No.: 15/313,856

(22) PCT Filed: Jul. 23, 2014

(86) PCT No.: PCT/US2014/047820
§ 371 (c)(1),
(2) Date: Nov. 23, 2016

(87) PCT Pub. No.: WO2016/014052
PCT Pub. Date: Jan. 28, 2016

(65) Prior Publication Data
US 2017/0203534 A1    Jul. 20, 2017

(51) Int. Cl.
*B32B 1/02* (2006.01)
*B32B 7/12* (2006.01)
(Continued)

(52) U.S. Cl.
CPC ............... *B32B 1/02* (2013.01); *A61M 5/002* (2013.01); *B32B 5/022* (2013.01); *B32B 7/12* (2013.01); *B32B 27/08* (2013.01); *B32B 27/10* (2013.01); *B32B 27/12* (2013.01); *B32B 27/32* (2013.01); *B32B 27/34* (2013.01); *B65D 75/5855* (2013.01); *B65D 85/70* (2013.01); *B32B 2270/00* (2013.01); *B32B 2307/31* (2013.01);
(Continued)

(58) Field of Classification Search
CPC .. B32B 1/02; B32B 7/12; B32B 27/08; B32B 27/32; B32B 27/10; B32B 27/12; B32B 27/34; B32B 5/022; B32B 2307/718; B32B 2270/00; B32B 2439/46; B32B 2307/31; B65D 75/5855; B65D 85/70; A61M 5/002
See application file for complete search history.

(56) References Cited

U.S. PATENT DOCUMENTS 5,567,533 A   10/1996 Toney
5,830,547 A   11/1998 MacKenzie et al.
(Continued)

FOREIGN PATENT DOCUMENTS

EP    2682419 A1    1/2014

*Primary Examiner* — Michael C Miggins
(74) *Attorney, Agent, or Firm* — Lynn M. Nett (57) ABSTRACT

The present invention is directed to a peel-open package having a first film comprising an exterior sealant layer comprising a polyolefin polymer resin and a fatty acid or a fatty acid derivative, and a second film comprising an exterior layer comprising paper or a nonwoven material. The paper or nonwoven material is adhered to the sealant layer of the first film to form a peelable interface therebetween and to enclose a product, to accordance with the present invention, the polyolefin sealant layer of the first film is heat sealed directly to the paper or nonwoven material of the second film to form a peelable seal which can be readily peeled without substantial release of free fibers form the paper or nonwoven material.

20 Claims, 4 Drawing Sheets

(51) Int. Cl.
*B32B 27/08* (2006.01)
*B32B 27/32* (2006.01)
*B32B 27/10* (2006.01)
*B32B 27/12* (2006.01)
*B32B 27/34* (2006.01)
*B32B 5/02* (2006.01)
*B65D 75/58* (2006.01)
*A61M 5/00* (2006.01)
*B65D 85/00* (2006.01)

(52) U.S. Cl.
CPC ..... *B32B 2307/718* (2013.01); *B32B 2439/46* (2013.01)

(56) References Cited

U.S. PATENT DOCUMENTS

| | | |
|---|---|---|
| 6,590,034 B2 | 7/2003 | Wanic et al. |
| 6,602,590 B2 | 8/2003 | Ting et al. |
| 6,630,237 B2 | 10/2003 | Rivett et al. |
| 6,632,521 B2 | 10/2003 | Christopherson et al. |
| 6,709,687 B2 | 3/2004 | Pockat et al. |
| 6,726,968 B2 | 4/2004 | Porter |
| 6,803,113 B2 | 10/2004 | Porter et al. |
| 6,893,672 B2 | 5/2005 | Ingraham |
| 7,863,383 B2 | 1/2011 | Gibbons et al. |
| 2002/0168489 A1 | 11/2002 | Ting et al. |
| 2003/0165646 A1 | 9/2003 | Porter |
| 2003/0198764 A1 | 10/2003 | Kendig |
| 2004/0234797 A1 | 11/2004 | Schwark et al. |
| 2005/0181205 A1 | 8/2005 | Story |
| 2006/0105126 A1 | 5/2006 | Kendig |
| 2008/0226855 A1 | 9/2008 | Shang et al. |

PEEL-OPEN PACKAGE

BACKGROUND OF THE INVENTION

The present invention relates generally to primary packaging and more particularly, to packages formed from polymeric films which are heat sealed to paper and/or non-woven materials to produce peel-open packages.

The use of heat sealable polymeric films is widely used in the packaging art. Direct heat sealing between polymeric films and paper or non-woven materials such as DuPont™ Tyvek® and the like, is attractive commercially because they can be formed by directly fusion heating of the outer surface of polymeric film to the paper or non-woven material. However, gaining access to articles which have been packaged by heat sealing films to themselves or to other substrates often presents problems due to the strengths of the seals which are produced. The force required to open the package must be comfortable for the end-user but still strong enough in order to avoid the accidental opening of the package during transportation, handling and storage of the same. For example, if the seals are to have sufficient strength to maintain their integrity, upon opening of the package, the sealed area of the package may exhibit linting, i.e., the release of loose fibers from paper or non-woven material resulting from peeling the polymeric film from the paper or non-woven material. Linting can especially be a problem in a sterile environment such as an operating room where the loose fibers can come into contact with a patient. For this reason, direct fusion seals between polymeric films and paper or non-woven materials for medical packaging applications must be provided without substantial release of free fibers when the package is peeled open.

This problem can be addressed by constructing polymeric films so that they fail within their respective structures when a peeling force is applied, such failure being by delamination of a multilayer polymeric film or by rupture within the thickness of a layer of the polymeric film. However, this film construction will often still result in high peel strengths which cause linting or tear in the paper or nonwoven. For applications where linting or tear is problematic, a coated paper or nonwoven is used. This method allows the applied coating to fail cohesively during peeling of the seal area, protecting the paper or nonwoven surface from linting or tear. However, coated paper and coated non-woven materials are significantly more expensive than their uncoated counter-parts.

Therefore, there is a definite need to provide direct fusion seals between polymeric films and uncoated paper or uncoated non-woven materials without experiencing the problems discussed above.

SUMMARY OF THE INVENTION

The present invention is directed to a peel-open package having a first film comprising an exterior sealant layer comprising a polyolefin polymer resin and a fatty acid or a fatty acid derivative, and a second film comprising an exterior layer comprising paper or a nonwoven material. The paper or nonwoven material is adhered to the sealant layer of the first film to form a peelable interface therebetween and to enclose a product. In accordance with the present invention, the polyolefin sealant layer of the first film is heat sealed directly to the paper or nonwoven material of the second film to form a peelable seal which can be readily peeled without substantial release of free fibers from the paper or nonwoven material. Peel strengths of the peelable seals can be controlled over a wide temperature range such that the first film can be peeled from the second film by application of a force of between 100 g/in to 300 g/in compared with those obtained for analogous heat seal interfaces where a fatty acid or a fatty acid derivative is not incorporated into or applied onto the first film of the package.

In one preferred embodiment, the fatty acid or fatty acid derivative is incorporated into the sealant layer and at least a portion of the same may migrate through this layer to the outer surface of the sealant layer. In a preferred embodiment, the fatty acid or fatty acid derivative is incorporated into the sealant layer and one or more interior layers proximal to the sealant layer and at least a portion of the fatty acid or fatty acid derivative may migrate through these layers to the outer surface of the sealant layer. In another preferred embodiment, the fatty acid or fatty acid derivative is applied onto the outer surface of the sealant layer. In still another preferred embodiment, the fatty acid or fatty acid derivative is incorporated into the sealant layer in an amount of between 0.01% and 2.5%, between 0.05% and 2.0%, or between 0.1% and 2.0% by weight relative to the total weight of the first layer. Alternatively, in another preferred embodiment, the fatty acid or fatty acid derivative is applied to onto the outer surface of the sealant layer in an amount of between 1.0 mg/m$^2$ and 500 mg/m$^2$, between 1.0 mg/m$^2$ and 250 mg/m$^2$, or between 1.0 mg/m$^2$ and 100 mg/m$^2$.

Heat seals formed between the first and second films in accordance with the present invention have also shown more consistent peel strengths over a sealing temperature range of between 127° C. and 171° C. (260° F. and 340° F.).

In addition to providing an easily openable package, the present invention provides a peel-open package which can be readily sterilized without adversely affecting the seal strengths of the seals of the package.

In one preferred embodiment of the present invention, a peel-open sterilizable package is obtained when an exterior sealant layer of a first film comprises a blend of a polyolefin resin and a fatty acid which is then heat sealed to an exterior layer of a second film which comprises an uncoated paper or an uncoated nonwoven material.

In one preferred embodiment of the present invention, a peel-open sterilizable package is obtained when an exterior sealant layer of a first film comprises a blend of a polyolefin resin and a mono-glyceride, a di-glyceride, or a tri-glyceride, or a mixture thereof which is then heat sealed to an exterior layer of a second film which comprises an uncoated paper or an uncoated nonwoven material.

In another preferred embodiment of the present invention, a peel-open sterilizable package is also obtained when an exterior sealant layer of a first film comprises a polyolefin resin and has a coating of a mono-glyceride, a di-glyceride, or a tri-glyceride or a mixture thereof applied to its surface which is then heat sealed to an exterior layer of a second film which comprises an uncoated paper or an uncoated nonwoven material.

In still another preferred embodiment, a peel-open sterilizable package is obtained when a mono-glyceride, a di-glyceride, or a tri-glyceride formed as a condensation product of glycerol and a fatty acid selected from the group consisting of arachidonic acid, docosahexaenoic acid, elaidic acid, eicosapentaenoic acid, erucic acid, linoleic acid, linoelaidic acid, α-linolenic acid, myristoleic acid, oleic acid, palmitoleic acid, sapienic acid, vaccenic acid, arachidic acid, behenic acid, capric acid, caprylic acid, cerotic acid, lauric acid, lignoceric acid, myristic acid, palmitic acid and stearic acid is either blended with a polyolefin resin in an exterior sealant layer of a first film or is coated onto an exterior surface of said exterior sealant layer which is then heat sealed to an exterior layer of a second film that comprises an uncoated paper or an uncoated nonwoven material.

BRIEF DESCRIPTION OF THE DRAWINGS

Further features and advantages of the present invention will become apparent from the following detailed description, taken in combination with the appended drawings, in which.

DETAILED DESCRIPTION OF THE INVENTION

Figure 1:
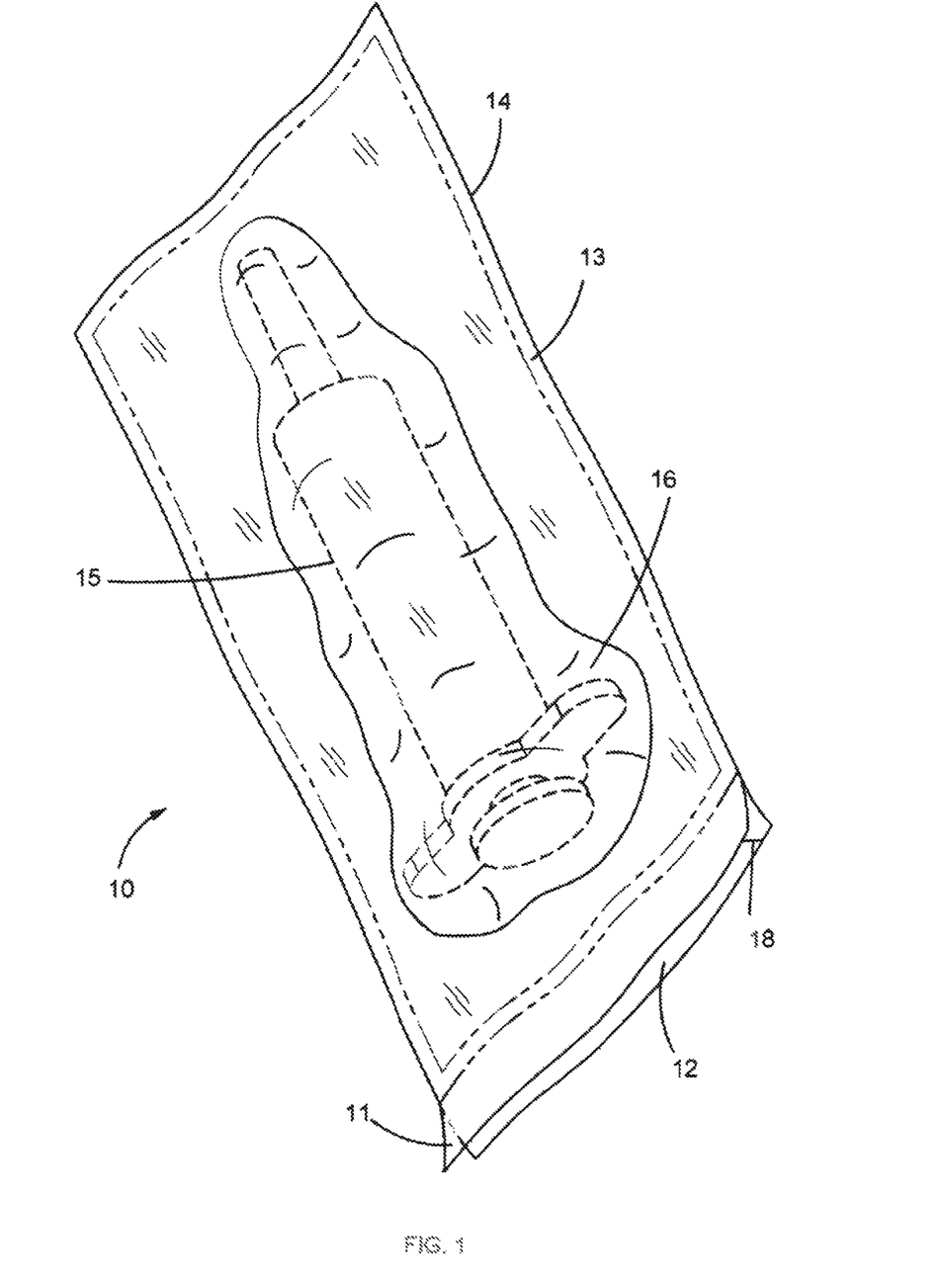
FIG. 1 illustrates a schematic view of one embodiment of a package according to the present invention in a closed state.
Figure 2:
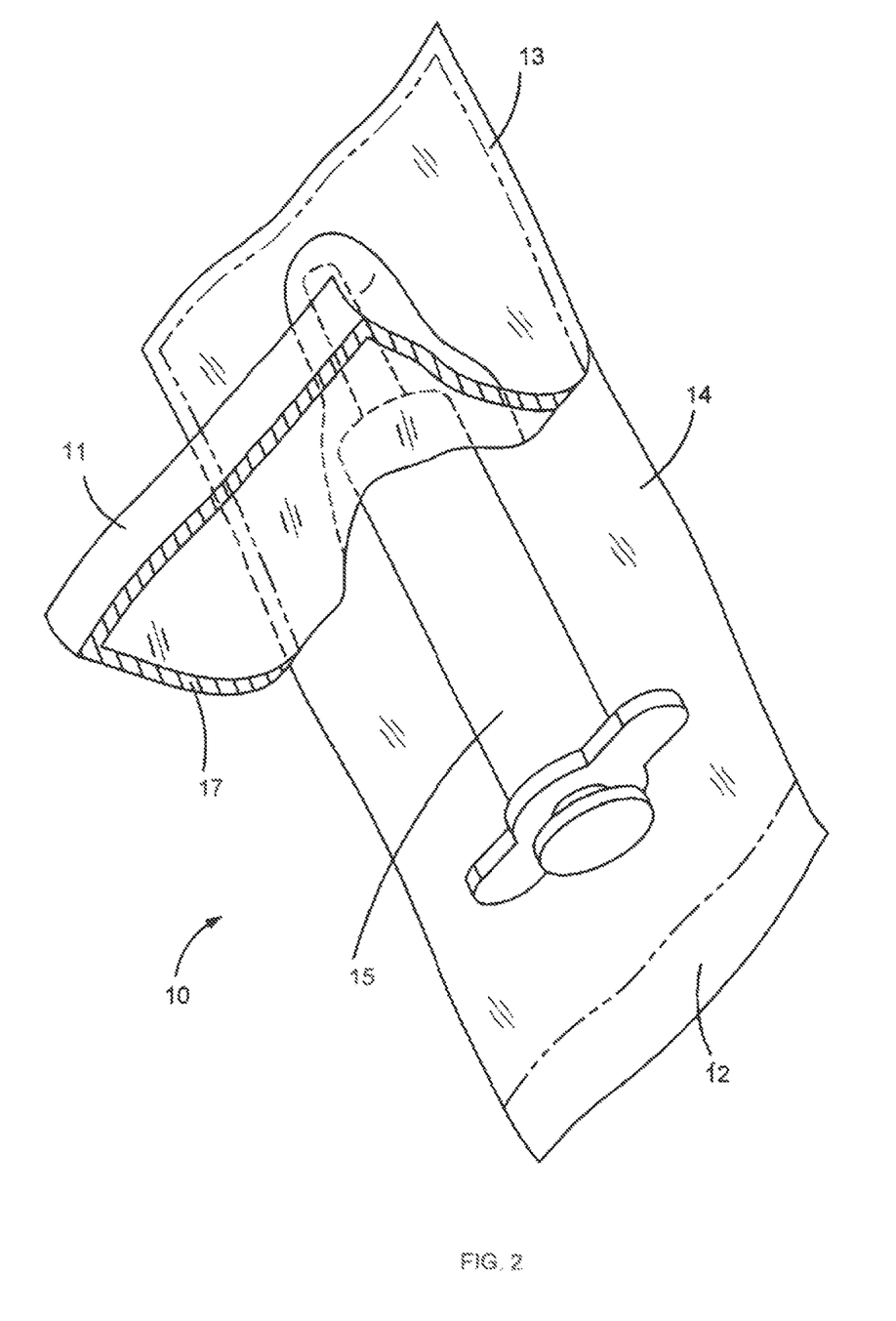
FIG. 2 illustrates a schematic view of one embodiment of a package according to the present invention in an opened state.

In accordance with the practice of the present invention, a representative peel-open package 10 as described herein is shown in FIGS. 1 and 2. Package 10 of the present invention comprises a thermoformed component 11 which is formed from a first film 100, and a lidding component 12 which is formed from a second film 200. The lidding component 12 is adhered to the thermoformed component 11 by a heat and pressure activated seal 13. The heat and pressure activated seal 13 is generally adjacent to a peripheral edge 14 of lidding component 12 and provides a border which surrounds a product cavity 15 for receiving a product 16.

In FIGS. 1-2, the product cavity 15 is formed into the general shape of the product 16 contained therein. Nevertheless, one skilled in the art would appreciate that the thermoformed component 11 may be formed into any shape as desired and may be of various sizes. Package 10 is particularly well suited for packaging of medical products such as, but not limited to, syringes and the like since the paper or nonwoven material of second film 200 is porous to gases such as ethylene oxide thus allowing the package contents to be sterilized prior to its ultimate use. It should be understood that peel-open package 10 may also package other products such as non-medical products including food items. While package 10 is depicted as having only one cavity 13, it is also contemplated that thermoformed component 11 of the present invention may include multiple cavities (not shown). While the packages depicted in FIGS. 1-2 are shown having a thermoformed component 11, it is also contemplated that the packages of the present invention include bags and pouches which are generally not thermoformed but have a flat component (not shown).

In order to open the peel-open package 10 of the present invention, the lidding component 12 is removed by peeling it away from the thermoformed component 11 to thereby provide access to the product 16 located therein as illustrated in FIG. 2. In accordance with an important aspect of the present invention, the lidding component 12 is peeled away from thermoformed component 11 without substantial release of paper fibers or nonwoven material fibers from second film 200. Because package 10 may contain a sterilized product 16, the ultimate end-user will typically expect to rely on the fact that the seal 13 has been maintained during shipment and that the sterilized object has not been contaminated. Therefore, another important feature of the present invention is that once the lidding component 12 is peeled away from thermoformed component 11, the heat seal 13 exhibits a cloudy, milky-white appearance 17 where the seal was maintained in order to provide evidence of the integrity of the seal prior to opening. In order to facilitate the end-user in the opening of package 10, there may optionally be included an un-sealed flange 18 where the thermoformed component 11 is not sealed to lidding component 12 so that the end-user can easily grasp the package and peel the thermoformed component 11 and the lidding component 12 in opposite directions.

EXAMPLES

As used herein, the term "sealant" refers to a layer which is heat sealable to itself or to other materials, i.e., be capable of fusion bonding by conventional heating means which generate sufficient heat on at least one film contact surface for conduction to the contiguous film contact surface and formation of a bond interface therebetween without loss of the film integrity. Advantageously, the bond interface must be sufficiently thermally stable to prevent gas or liquid leakage therethrough. Suitable examples of sealants for the present invention include, but are not limited to, polyolefins, including polyethylenes, polypropylenes, polybutylenes, ionomers, ethylene/α-olefin copolymers, ethylene/vinyl acetate copolymers and the like.

The term "fatty acid" as used herein refers to carboxylic acids with long hydrocarbon chains which may vary from 10-30 carbons (most usual is 12-18) which are either saturated or unsaturated. Unsaturated fatty acids have one or more double bonds between carbon atoms and include, but are not limited to arachidonic acid, docosahexaenoic acid, elaidic acid, eicosapentaenoic acid, erucic acid, linoleic acid, linoelaidic acid, α-linolenic acid, myristoleic acid, oleic acid, palmitoleic acid, sapienic acid and vaccenic acid. Saturated fatty acids have no double bonds between carbon atoms and include, but are not limited to arachidic acid, behenic acid, capric acid, caprylic acid, cerotic acid, lauric acid, lignoceric acid, myristic acid, palmitic acid and stearic acid. The term "fatty acid derivative" as used herein refers to esters and amides formed as a condensation product by reaction of one or more fatty acid with a monofunctional or polyfunctional alcohol and a monofunctional or polyfunctional amine, respectively. For example, esters may be a condensation product formed by partial or complete reaction of glycerol (a tri-functional alcohol) with one or more fatty acid to produce mono-glycerides, di-glycerides, and tri-glycerides.

The term "polyolefin" is used herein to mean a thermoplastic polymer derived from simple olefins having a methylene linkage between repeating units which may be formed by any method known to those skill in the art. Suitable examples of polyolefins include polyethylene ("PE"), low density polyethylene ("LDPE"), linear low density polyethylene ("LLDPE"), very low density polyethylene ("VLDPE"), ultra-low density polyethylene ("ULDPE"), medium density polyethylene ("MDPE"), high density polyethylene ("HDPE"), polyethylenes comprising copolymers of ethylene with one or more ethyhlene/alpha-olefins ("ethylene/α-olefins") such as butene-1, hexene-1, octene-1, or the like as a comonomer, ethylene/propylene copolymers, polypropylene, propylene/ethylene copolymer, polyisoprene, polybutylene, polybutene, poly-3-methylbutene-1, poly-4-methylpentene-1 ionomers and the like. Low density polyethylene ("LDPE") can be prepared at high pressure using free radical initiators, or in gas phase processes using Ziegler-Natty or vanadium catalysts, and typically has a density in the range of 0.916-0.940 g/cm³. LDPE is also known as "branched" or "heterogeneously branched' polyethylene because of the relatively large number of long chain branches extending from the main polymer backbone. Polyethylene in the same density range, i.e., 0.916 to 0.940 g/cm³, which is linear and does not contain long chain branching is also known; this linear low density polyethylene" ("LLDPE") can be produced with conventional Ziegler-Natta catalysts or with metallocene catalysts. As used in the present disclosure, the term "linear" is applied to a polymer that has a linear backbone and does not have long chain branching; i.e., a "linear" polymer is one that does not have the long chain branches. Relatively higher density LDPE, typically in the range of 0.928 to 0.940 g/cm³, is sometimes referred to as medium density polyethylene ("MDPE"). Polyethylenes having still greater density are the high density polyethylenes ("HDPEs"), i.e., polyethylenes having densities greater than 0.940 g/cm³, and are generally prepared with Ziegler-Natty catalysts. Very low density polyethylene ("VLDPE") is also known. VLDPEs can be produced by a number of different processes yielding polymers with different properties, but can be generally described as polyethylenes having a density less than 0.916 g/cm³, typically 0.890 to 0.915 g/cm³ or 0.900 to 0.915 g/cm³.

It should be understood that the phrase "tie layer material" may include, but not limited to, unmodified polyolefins such as polyethylenes and ethylene vinyl acetate copolymers, unmodified ester copolymers such as ethylene acrylate copolymers and ethylene methacrylate copolymers and unmodified ethylene acid copolymers such as ethylene acrylic acid copolymers and blends thereof. Tie layer materials may also include modified polyolefins including, but not limited to anhydride modified polyethylenes, maleic anhydride modified ethylene elastomers, anhydride modified ethylene vinyl acetate copolymers, modified ester copolymers such as anhydride modified ethylene acrylate copolymers, modified ethylene acid copolymers such as anhydride modified ethylene acrylic acid copolymers and blends thereof. Tie layer materials may further include a blend of an unmodified polyolefin or unmodified ester copolymer or unmodified ethylene acid copolymer and a modified polyolefin or modified ester copolymer or modified ethylene acid copolymer.

As used herein, the term "polyamide" refers to homopolymers, copolymers, or terpolymers having an amide linkage between monomer units which may be formed by any method known to those skilled in the art. Useful polyamide homopolymers include nylon 6 (polycaprolactam), nylon 11 (polyundecanolactam), nylon 12 (polylauryllactam), and the like. Other useful polyamide homopolymers also include nylon 4,2 (polytetramethylene ethylenediamide), nylon 4,6 (polytetramethylene adipamide), nylon 6,6 (polyhexamethylene adipamide), nylon 6,9 (polyhexamethylene azelamide), nylon 6,10 (polyhexamethylene sebacamide), nylon 6,12 (polyhexamethylene dodecanediamide), nylon 7,7 (polyheptamethylene pimelamide), nylon 8,8 (polyoctamethylene suberamide), nylon 9,9 (polynonamethylene azelamide), nylon 10,9 (polydecamethylene azelamide), nylon 12,12 (polydodecamethylene dodecanediamide), and the like. Useful polyamide copolymers include nylon 6,6/6 copolymer (polyhexamethylene adipamide/caprolactam copolymer), nylon 6/6,6 copolymer (polycaprolactam/hexamethylene adipamide copolymer), nylon 6,2/6,2 copolymer (polyhexamethylene ethylenediamide/hexamethylene ethylenediamide copolymer), nylon 6,6/6,9/6 copolymer (polyhexamethylene adipamide/hexamethylene azelaiamide/caprolactam copolymer), as well as other nylons which are not particularly delineated here. Exemplary of even more suitable polyamides include nylon 4,1, nylon 6,1, nylon 6,6/6I copolymer, nylon 6,6/6T copolymer, MXD6 (poly-m-xylylene adipamide), nylon 6T/6I copolymer, nylon 6/MXDT/I copolymer, nylon MXDI, poly-p-xylylene adipamide, polyhexamethylene terephthalamide, polydodecamethylene terephthalamide and the like.

Figure 3:
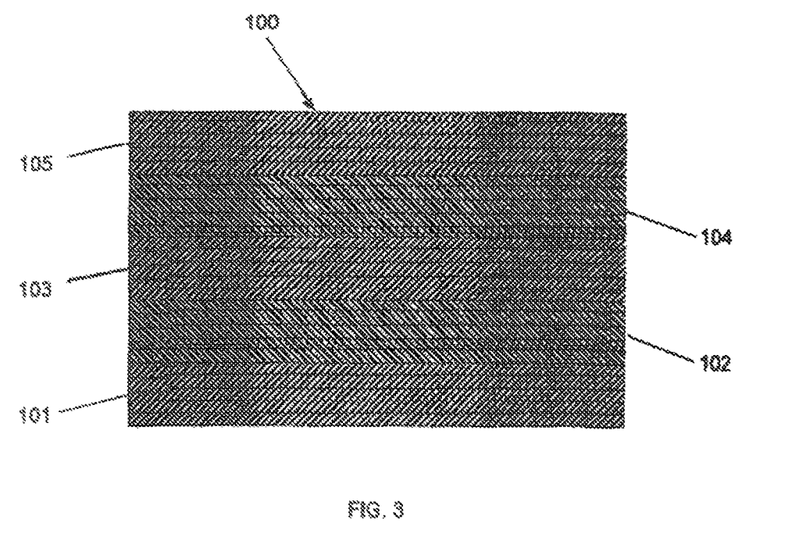
FIG. 3 illustrates a cross-sectional view of one embodiment of a first film of the present invention.

Referring now to FIG. 3, there is illustrated one preferred embodiment of a first film 100 having a five-layer structure according to the present invention. In this example, first film 100 includes an exterior sealant layer 101, a second layer 102 positioned adjacent to the exterior sealant layer 101 which comprises a blend of low density polyethylene and linear low density polyethylene resins, a third layer 103 positioned adjacent to second layer 102 and comprising a polyolefin, a fourth layer 104 positioned adjacent to the third layer 103 which comprises a tie material blend, and a fifth layer 105 positioned as an exterior layer adjacent to fourth layer 104 and comprising a polyamide resin. While this example of first film 100 is depicted as having five layers, it should be understood that first film 100 may be formed as a monolayer film comprising only the sealant layer 101. It is also contemplated that additional layers may be included beyond the five layers described herein.

In accordance with an important aspect of the present invention, the thermoformed component 11 is formed from a first film 100 comprising an exterior layer 101 comprising a fatty acid or a fatty acid derivative. In one preferred embodiment, the exterior layer of first film 100 comprises a polyolefin resin and a fatty acid derivative which includes a mono-glyceride, a di-glyceride, a tri-glyceride, or a mixture thereof. In a more preferred embodiment, the exterior layer of first film 100 comprises a polyolefin resin and includes a mono-glyceride, a di-glyceride, a tri-glyceride, or a mixture thereof formed from arachidonic acid, docosahexaenoic acid, elaidic acid, eicosapentaenoic acid, erucic acid, linoleic acid, linoelaidic acid, α-linolenic acid, myristoleic acid, oleic acid, palmitoleic acid, sapienic acid, vaccenic acid, arachidic acid, behenic acid, capric acid, caprylic acid, serotic acid, lauric acid, lignoceric acid, myristic acid, palmitic acid or stearic acid. In a most preferred embodiment, the exterior layer of first film 100 comprises a polyolefin resin and includes a mono-glyceride, a di-glyceride, a tri-glyceride, or a mixture thereof formed from oleic acid. Preferably, first film 100 is a coextruded multilayer film and in addition to the exterior sealant layer described above, has one or more film layers. The fatty acid and fatty acid derivative may be provided in a masterbatch with polyethylene, e.g., a masterbatch of 10% by weight of fatty acid or fatty acid derivative and 90% by weight polyethylene such as POLYBATCH® AF-1085 and POLYBATCH® AF-1088 from A. Schulman (Akron, Ohio, USA).

The total thickness of first film 100 of the present invention is generally from about 12.7 μm (0.5 mil) to about 254 μm (10 mil), most typically from about 25.4 μm (1 mil) to about 127 μm (5 mil).

Figure 4:
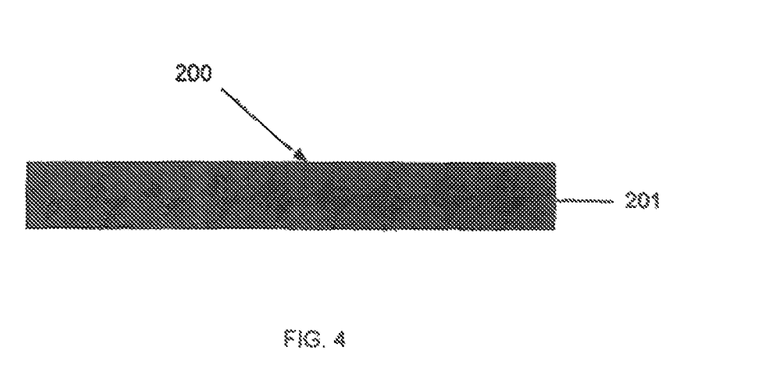
FIG. 4 illustrates a cross-sectional view of one embodiment of a second film of the present invention.

Referring now to FIG. 4, there is illustrated one preferred embodiment of a second film 200 having only an exterior layer 201 comprising a paper or a nonwoven material. Preferably, the paper or nonwoven material should be porous and have a sufficiently low pore size to prevent penetration by bacteria and other microbial organisms but with sufficiently high pore size to allow gases and/or water vapor to pass through the pores. The preferred materials for use as exterior layer 201 include, but are not limited to medical grade Kraft paper, especially, uncoated medical grade Kraft paper. A non-limiting example of such paper includes Arjo Ethypel® 60 gram/m² paper (Arjowiggins SAS, Boulogne Billancourt, France). Additional preferred materials for use as an exterior layer 201 include spunbonded nonwoven polyolefin such as, but are not, limited to DuPont™ Tyvek® (E. I. du Pont de Nemours and Company, Wilmington, Del., USA), especially, uncoated DuPont™ Tyvek®. Second film 200 may include any number of additional film layers depending upon the final requirements of the package.

Working Examples

In all the following examples, all film structures were produced using a cast co-extrusion and extrusion coating apparatuses, and methods which are well known to those skilled in the art. The cast co-extrusion film apparatus includes a multi-manifold flat die head for film through which the film composition is forced and formed into a flat sheet. The sheet is immediately quenched e.g., via cooled water bath, solid surface and/or air, and then formed into a film.

In the production of Example 1 as illustrated in FIG. 3, a first sub-portion of film 100 which corresponds to fifth layer 105, fourth layer 104 and third layer 103 was formed by cast co-extrusion methods. Then, a second sub-portion corresponding to second layer 102 and first layer 101 was extrusion coated onto the surface of third layer 103 of the first sub-portion to complete the final structure of film 100.

Example 1

Example 1 is one embodiment of a first film 100 of the present invention having a structure and layer compositions as described below and as illustrated in FIG. 3. Reported below is the thickness of the layer and the layer composition relative to the total weight of the layer.

Layer 101 (Sealant): 10μ (0.39 mil); 86.5 wt.-% of a low density polyethylene (LDPE)-Borealis FA6224 (Borealis AG, Vienna, Austria), 5 wt.-% of a 20%-active antiblock additive masterbatch in polyethylene-Ampacet 101820 (Ampacet Europe S.A., Windhof, Luxembourg), 4.5 wt.-% of a 3%-active slip additive masterbatch in polyethylene-PREMIX SL 104 (Premix Oy, Rajamäki, Finland); and 4 wt.-% of a 10%-active masterbatch of glyceryl monooleate in polyethlylene-Ampacet POLYBATCH® AF 1088 (A. Schulman, Inc., Akron, Ohio, USA). The amount of active glyceryl monooleate incorporated into the sealant layer was about 0.4 wt.-% relative to the total weight of this layer. It is believed that as much as 37 mg/m² of glyceryl monooleate may migrate to the outer surface of this layer over time.

Layer 102: 21μ (0.83 mil); 65 wt.-% of a linear low density polyethylene (LLDPE)-ExxonMobil™ LLDPE LL 1004YB (Exxon Mobil Corporation, Houston, Tex., USA) and 35 wt.-% of a low density polyethylene (LDPE)-DOW™ LDPE PG 7004 (Dow Chemical Corporation, Midland, Mich., USA).

Layer 103: 14μ (0.55 mil); 100 wt.-% of a low density polyethylene (LDPE)-ExxonMobil™ LDPE LD 151BW (Exxon Mobil Corporation, Houston, Tex., USA).

Layer 104: 5μ (0.2 mil); 80 wt.-% of a low density polyethylene (LDPE)-Borealis PE CA 7230 (Borealis AG, Vienna, Austria) and 20 wt.-% of an anhydride modified polyethylene-DuPont™ Byner 41E710 (E. I. du Pont de Nemours and Company, Wilmington, Del., USA).

Layer 105: 20μ (0.79 mil); 96 wt.-% of a polyamide (nylon 6)-Durethan B 40 FKA (Lanwess Corporation, Pittsburgh, Pa., USA) and 4 wt.-% of a 6%-active antiblock additive masterbatch in nylon 6-LUVOFILM 9706 (Lehmann & Voss & Company, Hamburg, Germany).

The film of Example 1 was then heat sealed to an uncoated medical grade Kraft paper (Arjo Ethyper® 60 g/m²) at various temperatures at 50 psi and a dwell time of 1.5 seconds. The peel strength of the seal between the sealant layer 101 of film 100 and the paper was measured at a 90° angle and the results are reported below in TABLE 1.

TABLE 1

| Sealing Temperature (° C.) | Seal Strength (grams/inch) | Seal Strength (Newton/meter) |
|---|---|---|
| 120 | 34 | 13 |
| 130 | 117 | 45 |
| 140 | 223 | 86 |
| 150 | 267 | 103 |
| 160 | 267 | 103 |
| 170 | 300 | 116 |

In the production of Example 2 as also illustrated in FIG. 3, a first sub-portion of film 100 which corresponds to fifth layer 105 and fourth layer 104 was formed by cast co-extrusion methods. Then, a second sub-portion corresponding to third layer 103, second layer 102 and first layer 101 were extrusion coated onto the surface of fourth layer 104 of the first sub-portion to complete the final structure of film 100.

Example 2

Example 2 is another embodiment of a first film 100 of the present invention having a structure, layer thicknesses and layer compositions as described below and as illustrated in FIG. 3. Reported below is the thickness of the layer and the layer composition relative to the total weight of the layer.

Layer 101 (Sealant): 10μ (0.39 mil): 72.8 wt.-% of a low density polyethylene (LDPE)-Borealis FA6224 (Borealis AG, Vienna, Austria), 20 wt.-% of a linear low density polyethylene (LLDPE)-Exceed™ 2718CB (Exxon Mobil Corporation, Houston, Tex., USA), and 7.2 wt.-% of a 10%-active masterbatch of glyceryl monooleate in polyethlylene-Ampacet POLYBATCH® AF 1088 (A. Schulman, Inc., Akron, Ohio, USA). The amount of active glyceryl monooleate incorporated into the sealant layer was about 0.7 wt.-% relative to the total weight of this layer.

It is believed that as much as 67 mg/m² of glyceryl monooleate may migrate to the outer surface of this layer over time.

Layer 102: 33.9μ (1.3 mil); 44.9 wt.-% of a low density polyethylene (LOPE)-DOW™ LOPE PG 7004 (Dow Chemical Corporation, Midland, Mich., USA), 50 wt.-% of a linear low density polyethylene (LLDPE)-ExxonMobil™ LLDPE LL 1004YB (Exxon Mobil Corporation, Houston, Tex., USA) and 5.1 wt.-% of a 10%-active masterbatch of glyceryl monooleate in polyethlylene-Ampacet POLYBATCH® AF 1088 (A. Schulman, Inc., Akron, Ohio, USA). The amount of active glyceryl monooleate incorporated into this layer was about 0.51 wt.-% relative to the total weight of this layer. It is believed that as much as 159 mg/m² of glyceryl monooleate may migrate to the outer surface of the sealant layer over time.

Layer 103: 6.5μ (0.25 mil); 80 wt.-% of a low density polyethylene (LDPE)-Borealis PE CA 7230 ((Borealis AG, Vienna, Austria) and 20 wt.-% of an anhydride modified polyethylene-DuPont™ Bynel® 41E710 (E. I. du Pont de Nemours and Company, Wilmington, Del. USA).

Layer 104: 3.6µ (0.14 mil); 100 wt.-% of a polyamide (nylon 6)-DSM Akulon® F132-E1 (Koninklijke DSM N. V., Heerlen, the Netherlands).

Layer 105: 14.4µ (0.55 mil); 99.4 wt.-% of a polyamide (nylon 6)-DSM Akulon® F132-E1 (Koninklijke DSM N.V., Heerlen, the Netherlands) and 0.6 wt.-% of a 6%-active antiblock additive masterbatch in nylon 6-LUVOFILM 9706 (Lehmann & Voss & Company, Hamburg, Germany).

The film of Example 2 was then heat sealed to an uncoated medical grade Kraft paper (Arjo Ethyper 60 g/m$^2$) at various temperatures under 50 psi and a dwell time of 1.5 seconds. The peel strength of the seal between the sealant layer 101 of film 100 and the paper sealed was measured at a 90° delamination angle and the results are reported below in TABLE 2.

TABLE 2

| Sealing Temperature (° C.) | Seal Strength (grams/inch) | Seal Strength (Newton/meter) |
|---|---|---|
| 127 | 56 | 22 |
| 132 | 63 | 24 |
| 140 | 82 | 32 |
| 149 | 81 | 31 |
| 157 | 88 | 34 |
| 166 | 89 | 34 |
| 177 | 120 | 46 |

Comparative Example 1

Comparative Example 1 had the same film structure, layer thicknesses and layer compositions as described above for Example 1 and illustrated in FIG. 3, except for sealant layer composition. The sealant layer composition of Comparative Example 1 included 90.5 wt.-% of a low density polyethylene (LDPE)-Borealis FA6224 (Borealis AG, Vienna, Austria), 5 wt.-% of a 20%-active antiblock additive masterbatch in polyethylene-Ampacet 101820 (Ampacet Europe S.A., Windhof, Luxembourg), and 4.5 wt.-% of a 3%-active slip additive masterbatch in polyethylene-PREMIX SL 104 (Premix Oy, Rajamäki, Finland). No fatty acid or fatty acid derivative was present in the sealant layer.

The film of Comparative Example 1 was then heat sealed to an uncoated medical grade Kraft paper (Arjo Ethypel® 60 g/m$^2$) at various temperatures at 50 psi and a dwell time of 1.5 seconds. The peel strength of the seal between the sealant layer 101 of film 100 and the paper was measured at a 90° angle and the results are reported below in TABLE 3.

TABLE 3

| Sealing Temperature (° C.) | Seal Strength (grams/inch) | Seal Strength (Newton/meter) |
|---|---|---|
| 120 | 10 | 4 |
| 130 | 269 | 104 |
| 140 | 293 | 113 |
| 150 | 337 | 130 |
| 160 | 352 | 136 |
| 170 | 394 | 152 |

Comparative Example 2

Comparative Example 2 had the same film structure, layer thicknesses and layer compositions as described above for Example 1, except for sealant layer composition. The sealant layer composition of Comparative Example 2 included 69 wt.-% of a low density polyethylene (LDPE)-Borealis FA6224 (Borealis AG, Vienna, Austria), 20 wt.-% of a polybutene (PB)-Polybutene-1 PB 8640M (LyondellBassell Industries Holdings, Houston, Tex., USA), 6 wt-% of a 20%-active antiblock additive masterbatch in polyethylene-Ampacet 101820 (Ampacet Europe S.A., Windhof, Luxembourg), and 5 wt.-% of a 3%-active slip additive masterbatch in polyethylene-PREMIX SL 104 (Premix Oy, Rajamäki; Finland). No fatty acid or fatty acid derivative was present in the sealant layer.

The film of Comparative Example 2 was then heat sealed to an uncoated medical grade Kraft paper (Arjo Ethypel® 60 g/m$^2$) at various temperatures at 50 psi and a dwell time of 1.5 seconds. The peel strength of the seal between the sealant layer 101 of film 100 and the paper was measured at a 90° angle and the results are reported below in TABLE 4.

TABLE 4

| Sealing Temperature (° C.) | Seal Strength (grams/inch) | Seal Strength (Newton/meter) |
|---|---|---|
| 120 | 148 | 57 |
| 130 | 316 | 122 |
| 140 | 484 | 189 |
| 150 | 557 | 215 |
| 160 | 547 | 211 |
| 170 | 508 | 196 |

Comparative Example 3

Comparative Example 3 had the same film structure, layer thicknesses and layer compositions as described above for Example 1, except for the sealant layer composition. The sealant layer composition of Comparative Example 3 included 58 wt.-% of a low density polyethylene (LDPE)-Borealis FA6224 (Borealis AG, Vienna, Austria), 30 wt.-% of a polybutene (PB)-Polybutene-1 PB 8640M (LyondellBassell Industries Holdings, Houston, Tex., USA), 6 wt.-% of a 20%-active antiblock additive masterbatch in polyethylene-Ampacet 101820 (Ampacet Europe S.A., Windhof, Luxembourg), and 6 wt.-% of a 3%-active slip additive masterbatch in polyethylene-PREMIX SL 104 (Premix Oy, Rajamäki, Finland). No fatty acid or fatty acid derivative was present in the sealant layer.

The film of Comparative Example 3 was then heat sealed to an uncoated medical grade Kraft paper (Arjo Ethypel® 60 g/m$^2$) at various temperatures at 50 psi and a dwell time of 1.5 seconds. The peel strength of seal between the sealant layer 101 of film 100 and the paper was measured at a 90° angle and the results are reported below in TABLE 5.

TABLE 5

| Sealing Temperature (° C.) | Seal Strength (grams/inch) | Seal Strength (Newton/meter) |
|---|---|---|
| 120 | 153 | 59 |
| 130 | 207 | 80 |
| 140 | 451 | 174 |
| 150 | 453 | 175 |
| 160 | 565 | 218 |
| 170 | 559 | 216 |

The packages of the present invention can be manufactured using methods known in the art. Generally, the cavities are thermoformed from the first film 100 of the present invention in-line just prior to filling the cavities with a product to be packaged. The lidding component or second film is then unwound from a roll and brought into contact with the formed and filled thermoformed component such that the heat-seal layer of the lidding component contacts the thermoformed component. The lidding and thermoformed components are heat sealed, typically using a heated platen. Some areas of the package may not be sealed to provide a starting point for peeling off the lidding component prior to removing the product. If the lidding component is not pre-printed, printing is generally done just before heat sealing, After heat-sealing, the individual packages may be perforated using methods known is the art so that they can removed at point of use.

The above description and examples illustrate certain embodiments of the present invention and are not to be interpreted as limiting. Selection of particular embodiments, combinations thereof, modifications, and adaptations of the various embodiments, conditions and parameters normally encountered in the art will be apparent to those skilled in the art and are deemed to be within the spirit and scope of the present invention.

What is claimed:

1. A peel-open package, comprising:
   a first film comprising an exterior sealant layer comprising:
   (a) a polyolefin polymer resin and
   (b) a fatty acid or a fatty acid derivative;
   a second film comprising an exterior layer comprising paper or a nonwoven material; wherein the paper or nonwoven material is directly adhered by a heat seal to the sealant layer of the first film to form a peelable interface therebetween and to enclose a product between the first film and the second film.

2. A package according to claim 1, wherein the paper and nonwoven material is uncoated.

3. A package according to claim 1, wherein the fatty acid derivative is glycerol monooleate.

4. A package according to claim 1, wherein the fatty acid or fatty acid derivative is present on the surface of the first film in an amount of between 1.0 mg/m$^2$ and 500 mg/m$^2$.

5. A package according to claim 1, wherein the fatty acid or fatty acid derivative is incorporated into the first film in an amount of between 0.01% and 2.5% by weight relative to the total weight of the first layer.

6. A package according to claim 1, wherein the peelable interface has a seal strength of between 100 g/in and 400 g/in when sealed at a temperature of between 127° C. and 171° C. (260° F. and 340° F.), at a pressure of 50 psi and a dwell time of 1.5 seconds.

7. A package according to claim 1, wherein the polyolefin polymer resin of the exterior sealant layer is a polyethylene resin.

8. A package according to claim 7, wherein the polyethylene resin is a low density polyethylene resin.

9. A package according to claim 1, wherein the fatty acid derivative is a mono-glyceride, a di-glyceride, a tri-glyceride, or a mixture thereof.

10. A package according to claim 9, wherein the mono-glyceride, the di-glyceride, or the tri-glyceride is a condensation product of glycerol and an acid selected from the group consisting of, arachidonic acid, docosahexaenoic acid, elaidic acid, eicosapentaenoic acid, erucic acid, linoleic acid, linoelaidic acid, α-linolenic acid, myristoleic acid, oleic acid, palmitoleic acid, sapienic acid and vaccenic acid.

11. A package according to claim 9, wherein the mono-glyceride, the di-glyceride, or the tri-glyceride is a condensation product of glycerol and an acid selected from the group consisting of arachidic acid, behenic acid, capric acid, caprylic acid, cerotic acid, lauric acid, lignoceric acid, myristic acid, palmitic acid and stearic acid.

12. A package according to claim 9, wherein the mono-glyceride, the di-glyceride, or the tri-glyceride is a condensation product of glycerol and oleic acid.

13. A package according to claim 1, wherein the first film comprises a second layer positioned adjacent to the exterior sealant layer and comprising a blend of low density polyethylene and linear low density polyethylene resins.

14. A package according to claim 13, wherein the first film comprises a third layer positioned adjacent to the second layer and comprising a tie material blend.

15. A package according to claim 14, wherein the tie material blend comprises an anhydride modified linear low density polyethylene resin.

16. A package according to claim 14, wherein the tie material blend comprises an anhydride modified linear low density polyethylene resin and a low density polyethylene resin.

17. A package according to claim 14, wherein the first film comprises a fourth layer positioned adjacent to the third layer and comprising a polyolefin resin.

18. A package according to claim 17, wherein the polyolefin resin of the fourth layer is a low density polyethylene.

19. A package according to claim 17, wherein the first film comprises a fifth layer positioned as a second exterior layer adjacent to the fourth layer and comprising a polyamide resin.

20. A package according to claim 19, wherein the polyamide resin is a nylon 6 resin.

* * * * *

UNITED STATES PATENT AND TRADEMARK OFFICE
CERTIFICATE OF CORRECTION

PATENT NO. : 10,011,086 B2
APPLICATION NO. : 15/313856
DATED : July 3, 2018
INVENTOR(S) : Hanna-Mari Lahti et al.

Page 1 of 1

It is certified that error appears in the above-identified patent and that said Letters Patent is hereby corrected as shown below:

In the Specification

In Column 5, Line 23, delete "Natty" and insert -- Natta --, therefor.

In Column 6, Line 6, delete "4,1, nylon 6,1," and insert -- 4,I, nylon 6,I, --, therefor.

In Column 7, Line 66, delete "Byner" and insert -- Bynel® --, therefor.

In Column 8, Line 7, delete "Ethyper®" and insert -- Ethypel® --, therefor.

In Column 9, Line 13, delete "Ethyper" and insert -- Ethypel® --, therefor.

Signed and Sealed this
Twelfth Day of November, 2019

Andrei Iancu
*Director of the United States Patent and Trademark Office*